United States Patent [19]

Case

[11] Patent Number: 4,634,549

[45] Date of Patent: Jan. 6, 1987

[54] HAY FRAGRANCE

[76] Inventor: Marion D. Case, Rte. 3, Box 1462, Lake Geneva, Wis. 53147

[21] Appl. No.: 781,743

[22] Filed: Sep. 30, 1985

[51] Int. Cl.[4] .......................... A61K 7/46; C11B 9/00

[52] U.S. Cl. .......................... 252/522 R; 252/522 A

[58] Field of Search .............. 252/522, 522 A, 522 R

[56] References Cited

U.S. PATENT DOCUMENTS

| | | | |
|---|---|---|---|
| 133,719 | 12/1872 | Percival | 252/522 |
| 243,510 | 6/1881 | Chesebrough | 252/522 |
| 409,859 | 8/1889 | Nellensteyn | 252/522 |
| 498,830 | 6/1893 | Watel | 252/522 |
| 2,383,517 | 8/1945 | Sandoz | 252/522 |
| 3,364,265 | 1/1968 | Klingel et al. | 252/522 |
| 4,250,099 | 2/1981 | Kaiser | 260/346.22 |

*Primary Examiner*—Werren B. Lone

*Attorney, Agent, or Firm*—Mathew R. P. Perrone, Jr.

[57] ABSTRACT

Fragrance from alfalfa or clover hay is isolated from the cut hay by soaking the hay in suitable solvent, or by synthetically reproducing reproducing the fragrance molecule in chemical process. The resulting fragrance may be used in standard cosmetics or other systems requiring fragrance.

19 Claims, No Drawings

HAY FRAGRANCE

BACKGROUND OF THE INVENTION

This invention relates to fragrances and uses thereof, and more particularly to the fragrance of hay and uses thereof.

The cosmetic industry is a highly competitive industry. This competition is especially evident in the field of fragrances such as those used in perfumes, colognes, soaps, or other items applied on the skin of a person, developing and using an attractive fragrance in products provides a competitive advantage to the first user.

One common fragrance, which is highly acceptable and pleasing, is that of hay—especially the alfalfa or clover varieties of hay. Yet, no one has been able to use the fragrance of hay in toiletries, perfumes, aftershave lotions, or similar products. Anyone who has traveled through the farm country side in during the hay season, can attest to the desirable smell of the cut hay. It is clearly desireable to use this hay aroma in a fragrance. However, use of this fragrance has yet to be developed for commercial purposes.

It is highly difficult to isolate a hay fragrance. Special process steps and efforts must be taken to isolate this fragrance. If the steps are not achieved in proper order, the fragrance will be lost. Accordingly, the desired process for isolating the hay fragrance is critical.

Thus, it is clearly desirable to have advantages of an isolated hay fragrance used in cosmetic preportions.

SUMMARY OF THE INVENTION

Therefore, an object of this invention is to provide a fragrance.

A further object of this invention is to provide a hay fragrance for use in cosmetics.

Yet another object of this invention is to provide a fragrance which can be isolated from the cut hay.

These and other objects of the invention are met by isolating the essence of the fragrance of cut hay and dispersing the result of the extract into a desired cosmetic.

DESCRIPTION OF THE PREFERRED EMBODIMENTS

Fragrance from alfalfa or clover hay is isolated from the cut hay by condensing vapors steam distillation process treatment of the hay, soaking the hay in suitable solvent, or by synthetically reproducing reproducing the fragrance molecule in chemical process. The resulting fragrance may be used in standard cosmetics.

The hay fragrance may be used for perfuming or flavoring products such as cosmetics. Cosmetics or toiletries include—but are not limited to—soaps, salves, powders, toothpaste, mouthwash, deodorants, shampoos, lotions, eau de toilette, eau de cologne and essences. Also, the fragrance can be used in washing agents, detergents, smoking articles, food stuffs, luxury consumables and drinks, and other typical items. The artificial fragrance as well as the synthetically produced fragrance is suitable for use in these compositions.

The concentrated fragrance need only be used in small amounts in the compositions. The desired amounts of fragrance may be determined empirically. Usually, the concentrated fragrance provides up to about ten percent by weight of the composition. More usually, concentrated fragrance provides up to about five percent by weight of the composition. Most usually, the concentrated fragrance provides about 0.01 to about 2 percent by weight of the composition.

Basically, it is found that the more freshly the cut hay is, the better the fragrance. Thus, it is desirable to cut and use the hay within three hundred fifty (350) hours. It is more desirable to cut and use the hay within two hundred fifty (250) hours. It is even more desirable to cut and use the hay within one hundred (100) hours. It is most desirable to cut and use the hay within thirty (30) hours. That means, the soaking of the hay in the solvent must be started within the desired time frame.

Typical solvents which may be used to isolate the hay fragrance from the hay include organic solvents such as alcohols, and aromatic solvents. Examples of such solvents include ethanol, toluene, xylene, isopropanol, sec-butanol, and sec-amyl alcohol. Other solvents suitable for use include alcohols, ethers, ketones, esters, hydrocarbon and halogenated hydrocarbons. However, if alcohols are used directly, the problem of isolating the fragrance from the other solvents is avoided. If the other solvents are used, it is desirable to isolate the fragrance and redisperse the compounds into the alcohol suitable for use in a cosmetic or other fragrance use.

Usually, up to about fifteen liters of solvent are used for each kilogram of hay. More preferrably about one to about twelve liters of solvent are used for each kilogram of hay. Even more preferrably about two to about ten liters of solvent are used for each kilogram of hay. Most preferrably about three to about five liters of solvent are used for each kilogram of hay.

In the steam distillation process, hay is placed in a pressure chamber with water. The chamber is heated for a period of time. A valve access to the chamber is opened to withdraw the vapors. The vapors are condensed to provide the hay smell. Usually the chamber is heated up to about 200° C. Preferrably, the chamber is heated in the range of 65° C. to 190° C. More preferrably, the chamber is heated in the range of 75° C. to 170° C. Most preferrably, the chamber is heated in the range of 85° C. to 150° C. The set forth temperature ranges provide the best yields for the fragrance.

Throughout the specification, the reference to most preferred or most preferrably indicates the best yield per unit of reactants used. The most preferred temperature range provides the best yields. The most preferred water to hay ratio provides the best yield. Combinations of the most preferred maximize the yield.

With the steam distillation process, hay is used with up to ten liters of water per kilogram of hay. Preferrably, hay is used with 0.1 to nine liters of water per kilogram of hay. More preferrably, hay is used with 0.3 to eight liters of water per kilogram of hay. Most preferrably, hay is used with 0.4 to seven liters of water per kilogram of hay.

The following examples are offered for the purpose of illustrating the invention. The examples are not intended to limit the invention. Unless otherwise specified all parts and percentages in the examples are by weight of the total solution.

EXAMPLE ONE

A suitable fragrance is formed by soaking one kilogram of alfalfa hay cut within 24 hours of the start of soaking in 3 liters of isopropyl alcohol. The hay is submersed in the isopropyl alcohol and so soaked for a period of 24 hours. The liquid is then decanted off. The resulting liquid has the hay smell as determined by 3 independent observers.

EXAMPLE TWO

The fragrance isolated from Example One is dispersed in a standard formulation of aftershave lotion in the amount of one part of fragrance per 100 parts of aftershave lotion. The aftershave lotion had the desired hay fragrance and provided an adequate aftershave lotion.

EXAMPLE THREE

The procedure of Example One is repeated but for the fact that a ½ kilogram of alfalfa hay is used. The resulting liquid has the hay smell as determined by 3 independent observers. However, the same 3 independent observers determined that the fragrance is not as strong as the fragrance of Example One.

EXAMPLE FOUR

The procedure of Example One is repeated using ethanol in place of isopropyl alcohol. The results are substantially similar to the results of Example One.

EXAMPLE FIVE

The procedure of Example One is repeated but for the use of clover hay instead of alfalfa hay. The resulting liquid has the clover hay smell.

A standard carrying agent for cologne consisting of ninety five (95%) percent water by weight and five (5%) percent by weight of the resulting liquid of Example One is added to the cologne base. The resulting hay smell provides for effective cologne of long lasting duration.

EXAMPLE SIX

The procedure of Example Five is repeated but for the fact that the cologne base is replaced with an after shave base and that the amount of the resulting liquid is reduced to one-half (½) of one (1%) percent. The results are substantially the same as in Example Five.

EXAMPLE SEVEN

The procedure of Example One is repeated but for the fact that the hay is cut and stored for 100 hours prior to soaking. The fragrance recovered has a smell less strong than that of Example One as determined by three independent observers.

EXAMPLE EIGHT

The procedure of Example One is repeated but for the fact that the solvent is toluene. The toluene is evaporated over a vacuum leaving a fragrance residue. The fragrance residue is dispersed in ethanol. The fragrance of Example One is present as determined by three independent observers, but not as strong as the fragrance of Example One.

EXAMPLE NINE

A suitable fragrance is formed by steam distillation of one kilogram of alfalfa hay cut within 24 hours of the start the distillation. The hay is placed in one liter of water in a pressure cooker having a valve outlet. The cooker is sealed and heated for one hour at 100° C. The valve is then opened. The vapors are collected and condensed. The resulting liquid as condensed from the vapors has the hay smell as determined by 3 independent observers.

EXAMPLE TEN

The procedure of Example Nine is repeated but for the use of two liters of water. The resulting liquid as condensed from the vapors has the hay smell as determined by 3 independent observers, but the smell is not as strong as the smell of Example Nine.

EXAMPLE ELEVEN

The condensed liquid of Example Nine is dispersed in an after shave lotion base at one percent by weight of the base. The after shave lotion is tested and found to be suitable.

Because of this disclosure and solely because of this disclosure, modifications of this inventions will become clear to a person having ordinary skill in this particular art. Such modifications are clearly covered hereby.

What is claimed and sought to be secured by Letters Patent of the United States is:

1. A method for isolating a hay fragrance from hay selected from the group consisting of alfalfa hay and clover hay comprising:

a. cutting said hay;

b. soaking said hay in at least one organic solvent selected from the group consisting of ethanol and isopropanol to form a liquid containing a hay fragrance, wherein up to about fifteen liters of said at least one organic solvent is used to soak each kilogram of said hay; and wherein said hay is soaked within 350 hours of said cutting of said hay;

c. recovering the said liquid containing a hay fragrance; and d. using said liquid to add said hay fragrance to a product selected from the group consisting of toiletries, perfumes, aftershave lotions, cosmetics soaps, salves, powders, toothpaste, mouthwash, deodorants, shampoos, lotions, eau de toilette, eau de cologne, essences, washing agents, detergents, smoking articles, food stuffs, luxury consumables and drinks.

2. The method of claim 1 wherein said product is at least one selected from the group consisting of cosmetics and toiletries.

3. The method of claim 2 wherein said product is selected from the group consisting of soaps, salves, powders, toothpaste, mouthwash, deodorants, shampoos, lotions, eau de toilette, eau de cologne and essences.

4. The method of claim 2 wherein said product is selected from the group consisting of washing agents, detergents, smoking articles, food stuffs, luxury consumables and drinks.

5. The method of claim 1 wherein a sufficient amount of said liquid is added to said product in an amount sufficient to provide a fragrance in in said product up to about ten percent by weight of said product.

6. The method of claim 5 wherein said natant liquid is added to said product in an amount of about 0.01 to about 2 percent by weight of said product.

7. The method of claim 1 wherein said hay is soaked within 100 hours of cutting said hay.

8. The method of claim 7 wherein said hay is soaked within 30 hours of cutting said hay.

9. The method of claim 8 wherein about 3 to about 15 liters of said at least one organic solvent is used to soak each kilogram of hay.

10. The method of claim 9 wherein:

a. said at least one organic solvent is selected from the group consisting of ethanol and isopropanol;

b. said hay is soaked within 30 hours of cutting said hay; and c. said natant liquid is added to said product in an amount of about 0.01 to about 2 percent by weight of said product.

11. The method of claim 10 wherein said hay is alfalfa hay.

12. The method of claim 10 wherein said hay is clover hay.

13. A method for isolating a hay fragrance from hay selected from the group consisting of alfalfa hay and clover hay comprising:

a. cutting said hay;

b. soaking said hay by a steam distillation process in pressure chamber with water to form fragrant vapors;

c. heating said pressure chamber at a temperature in the range of 85° C. to 150° C. for a period of up to five hours to form vapors of a hay fragrance;

d. recovering vapors from said chamber;

e. condensing said vapors to form a condensate; and f. dispersing said condensate in a product to provide a hay fragrance for said product said product being selected from the group consisting of toiletries, perfumes, aftershave lotions, cosmetics soaps, salves, powders, toothpaste, mouthwash, deodorants, shampoos, lotions, eau de toilette, eau de cologne, essences, washing agents, detergents, smoking articles, food stuffs, luxury consumables and drinks.

14. The method of claim 13 wherein a sufficient amount of said condensate is added to said product in an amount sufficient to provide a fragrance in in said product up to about ten percent by weight of said product.

15. The method of claim 14 wherein said condensate is added to said product in an amount of about 0.01 to about 2 percent by weight of said product.

16. The method of claim 15 wherein said hay is soaked within 350 hours of cutting said hay.

17. The method of claim '16 wherein said hay is soaked within 100 hours of cutting said hay.

18. The method of claim 17 wherein said hay is soaked within 30 hours of cutting said hay.

19. The product made by the method of claim 17.

* * * * *